US 6,696,058 B2

(12) United States Patent
Pellico et al.

(10) Patent No.: US 6,696,058 B2
(45) Date of Patent: Feb. 24, 2004

(54) AQUEOUS ENZYMATIC DENTURE ADHESIVES

(75) Inventors: Michael A. Pellico, Rancho Dominguez, CA (US); Harjinder Kang, Buena Park, CA (US)

(73) Assignee: Laclede, Inc., Rancho Dominguez, CA (US)

( * ) Notice: Subject to any disclaimer, the term of this patent is extended or adjusted under 35 U.S.C. 154(b) by 181 days.

(21) Appl. No.: 10/058,455

(22) Filed: Jan. 29, 2002

(65) Prior Publication Data

US 2003/0143214 A1 Jul. 31, 2003

(51) Int. Cl.[7] ............................................. A61K 38/44
(52) U.S. Cl. .................... 424/94.4; 424/50; 424/77; 424/94.2; 435/189; 435/192; 523/120
(58) Field of Search .................. 424/50, 77, 94.4, 424/94.2; 523/120; 435/189, 192

(56) References Cited

U.S. PATENT DOCUMENTS

| 3,962,107 | A | * | 6/1976 | Levin et al. | |
| 4,150,113 | A | | 4/1979 | Hoogendorn | 424/50 |
| 4,178,362 | A | | 12/1979 | Hoogendorn | 424/48 |
| 4,269,822 | A | | 5/1981 | Pellico | 424/50 |
| 4,518,721 | A | | 5/1985 | Dhabhar et al. | 523/120 |
| 4,537,764 | A | | 8/1985 | Pellico | 424/50 |
| 4,564,519 | A | | 1/1986 | Pellico | 424/48 |
| 4,576,817 | A | | 3/1986 | Montgomery | 424/94 |
| 4,578,265 | A | | 3/1986 | Pellico et al. | 424/50 |
| 4,617,190 | A | | 10/1986 | Montgomery | 426/61 |
| 4,804,412 | A | | 2/1989 | Komiyama et al. | 106/35 |
| 5,176,899 | A | | 1/1993 | Montgomery | 424/50 |
| 5,336,494 | A | | 8/1994 | Pellico | 424/94.4 |
| 5,453,284 | A | | 9/1995 | Pellico | 424/94.4 |
| 5,486,304 | A | * | 1/1996 | Eoga et al. | |
| 5,760,102 | A | | 6/1998 | Hall et al. | 523/120 |
| 5,989,526 | A | | 11/1999 | Aaslyng et al. | |
| 6,294,594 | B1 | | 9/2001 | Borj et al. | 523/120 |

* cited by examiner

Primary Examiner—Leon B. Lankford, Jr.
(74) Attorney, Agent, or Firm—Donald Diamond

(57) ABSTRACT

Hydro-activated and/or oxygen activated aqueous, enzymatic, antimicrobials denture adhesive compositions are stabilized against enzymatic action prior to oral application of the adhesive by incorporating a thickener into the adhesive formulation so as to provide the forrmulation with an enzyme immobilizing viscosity which inhibits enzymatic action during processing and in the adhesive package. An illustrative, thickened, enzymatic adhesive with this enhancement contains glucose oxidase, glucose, lactoperoxidase and potassium thiocyanate together with a mixture of polyacrylic acid and polyvinylpyrrolidone in an amount to provide the adhesive with a viscosity of at least about 300,000 centipoises.

16 Claims, No Drawings

AQUEOUS ENZYMATIC DENTURE ADHESIVES

BACKGROUND OF THE INVENTION

1. Field of the Invention

This invention relates to enzymatic denture adhesive compositions and, more particulary, to stabilized, aqueous, enzymatic denture adhesives, which, upon oral application, produce an anti-bacterial and bacteriostatic effect in the oral cavity by activation of the enzyme system within the adhesive.

Denture adhesives are used by denture wearers to secure loose fitting dentures. When a denture is first made, it fits tightly in the mouth. However, with the passage of time, the mouth changes and the denture often becomes less secure, with loss of the initial tight fit.

When this occurs, the patient has three choices: (a) obtain a new denture, (b) reline the old denture, or (c) use a denture adhesive. For those who choose denture adhesives, there are diverse products from which a selection can be made. These include powders, gels, pastes, and sheets. The adhesives are based on water soluble gums and polymers such as carboxymethyl cellulose, gum arcacia, gum tragacanth, poly (ethylene oxide), polyvinylpyrrolidone, vinyl methyl ether maleic anhydride, polyacrylamides, acetic polyvinyl compounds, polyacrylic acid derivates and the like.

The most common denture adhesives are those sold as pastes. The pastes are usually a combination of gums and powders combined with oil and/or other vehicle. The denture wearer squeezes the paste from a dispensing tube onto the denture which is then fitted into the mouth. Denture powders based on gums and/or polymers are also widely used by sprinkling the powder onto the denture which is then positioned in the mouth. Denture adhesives are also sold as sheets or films prepared from gums or polymers.

Regardless of the physical form of these adhesives, they all require contact with water to become effective. It is only when the gums and polymers become wet that they develop their adhesive properties. Normally, these adhesives work very well in the mouth. However, for denture wearers who suffer from dry mouth (xerostomia), dentures adesives work poorly or not at all because there is insufficient saliva to activate these adhesives, Also, because saliva is naturally antibacterial, people who suffer from dry mouth have an increased risk of periodontal disease, cavities and mouth odors.

The invention herein is directed to water-based denture adhesive compositions which incorporate (a) a hydro-activated anti-bacterial enzyme system and (b) a thickener so as to provide the composition with an enzyme immobilizing visvosity to inhibit enzymatic action during processing and in the denture adhesive package prior to oral application. The aqueous denture adhesive, with its anti-bacterial system, is particularly well suited for denture wearers who suffer from impaired saliva flow and provides those denture users with oral protection that would otherwise be present with normal saliva flow.

2. Related Art

2A. Enzyme Systems

It is disclosed in the prior art that enzymatic anti-bacterial systems, predicated on oxidoreductase enzymes such as glucose oxidase, can be incorporated into oral care products and other products such as powder milk (U.S. Pat. No. 4,617,190) and bandages (U.S. Pat. No. 4,576,817) for producing an anti-bacterial effect in a defined environment.

U.S. Pat. No. 4,150,113 (Hoogendoorn et al., 1979) and U.S. Pat. No. 4,178,362 (Hoogendorn et al., 1979) disclose, respectively, an enzymatic toothpaste and an enzymatic chewable dentifrice containing glucose oxidase which acts on glucose present in saliva and tooth plaque to produce hydrogen peroxide. The patentees note that oral bacteria, through enzyme systems having SH-Groups, effect glycolysis of food products containing sugars and point out that lactoperoxidase, which is present in saliva, provides the means for transferring oxygen from hydrogen peroxide to oral bacteria resulting in the oxidation of the SH-containing enzymes into inactive disulfide enzymes. It is further disclosed that the dentifrice may be formulated with potassium thiocyanate.

U.S. Pat. No. 4,269,822 (Pellico et al., 1981) discloses an antiseptic dentifrice containing an oxidizable amino acid substrate and an oxidoreductase enzyme specific to such substrate for producing hydrogen peroxide and ammonia upon oral application of the dentifrice, with pre-application stability being maintained by limiting the quantity of any water present in the dentifrice.

U.S. Pat. No. 4,537,764 (Pellico et al., 1985) discloses an enzymatic dentifrice containing Beta-D-glucose and glucose oxidase for producing hydrogen peroxide upon oral application of the dentifrice, with pre-application stability being maintained by limiting any water in the dentifrice to not more than about 10 wt. % based on the weight of the dentifrice.

U.S. Pat. No. 4,564,519 (Pellico et al., 1986) discloses a di-enzymatic chewable dentifrice which contains, for example, glucose and glucose oxidase for producing hydrogen peroxide upon chewing the dentifrice and further contains a thiocyanate salt and lactoperoxidase for interacting with hydrogen peroxide to produce a hypothiocyanate (sic) bacterial inhibitor, with pre-application stability being maintained by limiting any unbound water in the chewable dentifrice to an amount not more than about 1.0 wt. % and limiting the total water, bound and unbound, to not more than about 10 wt. %.

U.S. Pat. No. 4,578,365 (Pellico et al., 1986) discloses a di-enzymatic dentifrice which contains, for example, glucose and glucose oxidase for producing hydrogen peroxide upon oral application of the dentifrice and further contains a thiocyanate salt and lactoperoxidase for interacting with hydrogen peroxide to produce a hypothiocyanate (sic) with pre-application stability being maintained by limiting any water in the dentifrice to not more than about 10 wt. % based on the weight of the dentifrice.

U.S. Pat. No. 5,176,899 (Montgomery, 1993) discloses an aqueous enzymatic dentifrice which contains, for example, Beta-D-Glucose and glucose oxidase for producing hydrogen peroxide upon oral application of the dentifrice and, optionally, contains a thiocyanate salt and lactoperoxidase for interacting with hydrogen peroxide to produce a hypothiocyanite (OSCN—) bacteriostatic agent, with pre-application stability being maintained by processing and packaging the dentifrice under vacuum conditions so as to limit the level of dissolved oxygen in the dentifrice.

U.S. Pat. No. 5,336,494 (Pellico, 1994) discloses an orally chewable, enzymatically coated pet product which contains, for example, Beta-D-glucose and glucose oxidase for producing hydrogen peroxide upon oral chewing of the product and may further contain a peroxidase and an alkali metal salt of an oxygen accepting anion such as potassium iodide for interacting with hydrogen peroxide to produce hypoiodite, an anionic bacterial inhibitor.

U.S. Pat. No. 5,453,284 (Pellico, 1995) discloses an aqueous enzymatic dentifrice having a water content in excess of 10 wt. % and which contains, for example, Beta-D-glucose and glucose oxidase for producing hydrogen peroxide upon oral application of the dentifrice and may further contain a peroxidase and an oxidizable alkali metal salt such as the thiocyanate, chloride or iodide salt of sodium or potassium for interacting with hydrogen peroxide to produce an anionic bacterial inhibitor, with pre-application stability being maintained by the addition of a water soluble thickener in an amount to provide the dentifrice with a viscosity from about 800 to about 75,000 centipoises.

2B. Denture Adhesives

U.S. Pat. No. 4,518,721 (Dhabhar et al., 1985) discloses a hydrophillic denture adhesive containing sodium carboxymethylcellulose, poly(ethylene oxide), polyethylene glycol and glycerin.

U.S. Pat. No. 4,804,412 (Komiyama, 1989) discloses a denture adhesive containing polyvinyl acetate and polypropylene oxide and which may further include other ingredients such as enzymes, as for example, dextranase, mutanase, levanase and in(s)ulinase.

U.S. Pat. No. 5,760,102 (Hall et al., 1998) discloses an aqueous denture adhesive containing aloe extract, polyvinylpyrrolidone, hydroxyethylcellulose, hydrogen peroxide and water.

U.S. Pat. No. 6,294,594 (Borja, 2001) discloses a denture cream formulation containing polyvinylpyrrolidone, poly(ethylene oxide), carboxymethylcellulose, mineral oil, petrolatum, polyacrylic acid derivative, silicon dioxide, flavor and dye.

Each of the foregoing patent references is incorporated herein by reference thereto.

SUMMARY OF THE INVENTION

In accordance with this invention, there is provided an aqueous enzymatic denture adhesive having a water content of at least about 10 wt. % and containing, per gram of adhesive, from about 0.015 to about 0.6 millimole of oxidizable substrate and from about 0.5 to about 5,000 International Units of oxidoreductase enzyme specific to such substrate for producing hydrogen peroxide upon oral application of the adhesive, and further containing non-toxic, ambient, water soluble thickener in an amount to provide the adhesive with a viscosity from about 300,000 to about 1,900,000 to therby stabilize the adhesive against the production of hydrogen peroxide prior to oral application of the adhesive.

DETAILED DESCRIPTION

The invention described herein is directed to the use of thickener in aqueous denture adhesive compositions containing hydro-activated and/or oxygen activated antibacterial enzyme system to thereby provide a viscosity which inhibits the enzymatic reaction prior to oral application of the adhesive.

The thickeners which can be used in the practice of this invention comprise non-toxic, water soluble hydrocolloids and synthetic polymers as, for example, (a) water soluble gums such as gum arabic, gum tragacanth, gum karaya or gum guar; (b) microbial fermentation hydrocolloids such as xanthan gum; (c) starch derivatives such as high viscosity starch or hydrogenated starch; (d) cellulose derivatives such as sodium carboxymethylcellulose or hydroxymethylcellulose; and (e) synthetic polymers/gums including (i) vinyl polymers such as polyvinylpyrrolidone, polyviny lalcohol and carboxyvinyl polymer, (ii) acrylic polymers such as polyacrylic acid and polyacrylamide, and (iii) ethylene oxide polymers. A particular effective thickener is a combination of polyacrylic acid and polyvinylpyrrolidone which may be further enhanced by the presence of hydrogenated starch.

The thickener is generally present in an amount to provide the enzymatic denture adhesive with a viscosity from about 300,000 to about 1,900,000 centipoises, with an intermediate amount being so selected as to provide the adhesive with a viscosity from about 400,000 to about 1,750,000 centipoises, and a preferred amount being so selected as to provide the adhesive with a viscosity from about 600,000 to about 1,600,000 centipoises. Viscosity determinations can be made by utilizing a suitable viscometer in accordance with applicable procedures well known in the art.

The enzymatic component of the therapeutic composition comprises a first enzyme system containing an oxidizable substrate and an oxidoreductase enzyme specific to such substrate for producing hydrogen peroxide upon oral application of the adhesive, with the chemical environment of the oral cavity providing the source of additional reactant (oxygen) or reactants (oxygen, water) to effect the enzymatic reaction. Illustrative examples of oxidoreductase enzymes and their corresponding oxidizable substrates are set forth in the following table:

TABLE A

| OXIDOREDUCTASE ENZYME | OXIDIZABLE SUBSTRATE |
| --- | --- |
| Glucose oxidase | B-D-glucose |
| Hexose Oxidase | Hexose |
| Galactose Oxidase | D-galactose |
| Pyranose Oxidase | Pyranose |
| Pyruvate Oxidase | Pyruvate |
| Oxalate Oxidase | Oxalate |
| DL-Aminoacid Oxidase | DL-Aminoacid |

In an illustrative reaction, glucose oxidase catalyzes the interaction of Beta-D-glucose, water and oxygen during oral application of the adhesive to produce hydrogen peroxide and gluconic acid.

Glucose oxidase is characterized in the literature as a glycoprotein containing two molecules of flavine-adenine dinucleotide which has a molecular weight of approximately 150,000, an isoelectric point at pH 4.2 and an optimum pH at 5.5 with a broad pH range from 4 through 7.

The oxidizable substrate is generally present in the adhesive composition in an amount from about 0.015 to about 0.6 millimole per gram of adhesive composition and, preferably, in an amount from about 0.025 to about 0.1 millimole per gram of adhesive composition while the oxidoreductase enzyme specific to the substrate is generally present in the composition in an amount from about 0.5 to about 500 International Units (herein sometimes abbreviated IU) per gram of composition, and, preferably, in an amount from about 10 to about 40 IU per gram of composition. The term millimole identifies that quantity in grams corresponding to the molecular weight of the composition divided by one thousand. The term International Unit(s) identifies that amount of enzyme that will effect catalysis of 1.0 micromole of substrate per unit at pH 7.0 and 25 C. Oxidoreductase enzymes are supplied in dry or liquid form with the label specifying the concentration in International Units on a per gram or per milliliter, as appropriate.

In addition to the first enzyme system comprising oxidizable substrate and oxidoreductase enzyme specific to such substrate for producing hydrogen peroxide, the enzymatic adhesive composition of this invention is provided with a second enzyme system containing a peroxidatic peroxidase and an alkali metal salt of an oxygen accepting anion for interacting with hydrogen peroxide to produce an oxidized anionic bacterial inhibitor.

Peroxidases which can be used in the practice of this invention include lactoperoxidase, horseradish peroxidase, iodide peroxidase, and myeloperoxidase. Oxidizable salts which can be used in the practice of this invention include, for example, the thiocyanate, chloride or iodide salt of sodium, potassium, ammonium, calcium or magnesium or mixtures of such salts. In the presence of hydrogen peroxide, the oxygen accepting anion of the aforesaid salts, namely, thiocyanate, chloride or iodide, are oxidized to hypothiocyanite, hypochlorite and hypoiodite, respetively.

Lactoperoxidase is a glycoprotein which, in one commercial embodiment, is a lyophilized powder derived from milk. This commercial peroxidase has an activity of 80 IU/mg and a projected molecular weight of 93,000 for L-Tyrosine Iodination. The physical-chemical properties reported for lactoperoxidase include: molecular weight 78,000; partial specific volume 0.74; and heme/mole 1.0.

The peroxidase is generally present in the adhesive composition in an amount from about 0.05 to about 20 International Units per gram of composition and, preferably, in an amount from about 0.1 to about 1.0 International Units per gram of composition while the oxidizable salt is generally present in the composition in an amount from about 0.0001 to about 0.01 millimole per gram of composition and, preferably, in an amount from about 0.001 to about 0.006 millimole per gram of composition.

The operable integrity of the enzymatic system can be affected by catalase which is present in commercial glucose oxidase as well as mucous membrane tissue. Catalase, which is extraneous to the enzymatic system of this invention, competes with peroxidatic peroxidase for hydrogen peroxide. In order to reduce loss of hydrogen peroxide through the presence of catalase, an effective amount of enzymatic inhibitor specific to catalase can be advavtagelously incorporated into the enzymatic adhesive. An ascorbic salt such as sodium ascorbate, potassium ascorbate, ascorbyl palmitate, or mixtures thereof can be used as an enzymatic inhibitor which is specific to catalase. An effective amount of ascorbate salt for catalase inhibition is from about 0.000001 to about 0.0001 millimole per gram of adhesive composition. Iron salts such as ferrous sulfate can be incorporated the enzymatic composition as a potentiator for ascorbate salt in its role as catalase inhibitor.

The enzymatic adhesive compositions of this invention may advantageously be formulated with an aminohexose as, for example, an aminoglucose such as glucosamine, N-actyl glucosamine or mixtures thereof in order to increase the yield or accumulation of oxidized anionic bacterial inhibitor. The aminoglucose is generally present in the enzymatic composition in an amount from about 0.0001 to about 0.002 millimole per gram of adhesive and, preferably, in amount from about 0.003 to about 0.001 millimole per gram of adhesive.

As As a result of the high viscosity of the enzymatic adhesives provided by the thickeners, the adhesives can be formulated with water in excess of 10 wt. % without initiating an enzymatic reaction prior to oral application of the adhesive. Water is generally present in the enzymatic adhesive in an amount from about 10 wt. % to about 60 wt. %, with an intermediate amount being from about 10 wt. % to about 50 wt. % and a preferred amount being from about 15 wt. % to about 35 wt. %.

In addition to the thickeners, enzyme system and water, the adhesive compositions of this invention may contain typical formulating ingredients such as humectants, buffering agents, fluorides, flavors, colors and sweeteners as well as a variety of auxiliary adhesive components as described in the above identified patents, the disclosures of which are incorporated by reference, together with the limitations as specified therein.

The enzymztic adhesives, in the form of a paste or gel, can be prepared in any suitable manner as, for example, by blending the dry ingredients into the liquid ingredients, with agitation, until a smooth mixture is obtained, with the proviso that shear sensitive ingredients, which include the enzymes, are added last to minize shear impact on such ingredients.

In accordance with this invention, it has now been found that oxidoreductase enzyme stability can be maintained in an aqueous denture adhesive that contains in excess of 10 wt. % water, as shown by the examples hereinafter set forth, when a thickener is used in the aqueous adhesive so as to provide a viscosity of at least about 300,000 centipoises.

EXAMPLE 1

This example illustrates an aqueous, enzymatic denture adhesive containing 10 wt. % water together with an enzyme system containing Beta-D-glucose, glucose oxidase, lactoperoxidase and potassium thiocyanate.

| Composition | Weight, grams |
|---|---|
| Glycerine | 77.0000 |
| D.I. Water | 10.0000 |
| Xanthan gum | 4.0000 |
| Carboxymethylcellulose | 8.0000 |
| Lactoperoxidase (100 IU/mg) | 0.0005 (50 IU) |
| Beta-D-glucose | 1.0000 |
| Glucose oxidase (100 IU) | 0.0010 (100 IU) |
| Potassium thiocyanate | 0.1500 |
| | 100.1515 |

The viscosity of this enzymatic adhesive is 300,000 centipoises and the adhesive has an enzymatic shelf life in excess of 2 years.

EXAMPLE 2

This example illustrates an aqueous, enzymatic denture adhesive containing 15 wt. % water together with an enzyme system containing Beta-D-glucose, glucose oxidase, lactoperoxidase and potassium thiocyanate wherein the thickener is a combination of polyacrylic acid (Carbopol 980) and hydroxymethyl cellulose.

| Composition | Weight, grams |
|---|---|
| Glycerine | 42.0000 |
| Sorbitol (70% solids, 30% water) | 50.0000 |
| Carbopol 980 | 3.0000 |
| Hydroxymethylcellulose | 3.0000 |
| Beta-D-glucose | 1.0000 |
| Lactoperoxidase (100 IU/mg) | 0.0005 (50 IU) |
| Glucose oxidase (100 IU) | 0.0010 (100 IU) |

-continued

| Composition | Weight, grams |
|---|---|
| Potassium thiocyanate | 0.1500 |
| Sodium hydroxide | 1.0000 |
| | 100.1515 |

The viscosity of this enzymatic adhesive is 400,000 centipoises and the adhesive has an enzymatic shelf life in excess of 3 years.

EXAMPLE 3

This example illustrates an aqueous, enzymatic denture adhesive containing 10 wt. % water together with an enzyme system containing hexose, hexose oxidase, myeloperoxidase and potassium thiocyanate wherein the thickener is a combination of polyacrylic acid (Carbopol 980) and hydrogenated starch.

| Composition | Weight, grams | |
|---|---|---|
| Glycerine | 10.0000 | |
| D.I. Water | 10.0000 | |
| Hydrogenated starch | 67.0000 | |
| Carbopol 980 | 4.0000 | |
| Hexose (100 IU/mg) | 7.0000 | |
| Hexose oxidase (100 IU/mg) | 0.0001 | (10 IU) |
| Myeloperoxidase (100 IUmg) | 0.0002 | (100 IU) |
| Potassium thiocyanate | 0.1500 | |
| Sodium hydroxide | 2.0000 | |
| | 100.1503 | |

The viscosity of this enzymatic adhesive is 600,000 centipoises and the adhesive has an enzymatic shelf life in excess of 2 years.

EXAMPLE 4

This example illustrates an aqueous, enzymatic denture adhesive containing 57 wt. % water together with an enzyme system containing Beta-D-glucose, glucose oxidase, myeloperoxidase and potassium thiocyanate wherein the thickener is a combination of polyacrylic acid (Carbopol 980) and hydrogenated starch.

| Composition | Weight, grams | |
|---|---|---|
| D.I. Water | 57.000 | |
| Hydrogenated starch | 27.000 | |
| Carbopol 980 | 2.000 | |
| Polyvinylpyrrolidone | 8.000 | |
| Beta-D-glucose | 5.000 | |
| Glucose oxidase (100/IU/mg) | 0.005 | (500 IU) |
| Myeloperoxidase (100/IUmg) | 0.001 | (100 IU) |
| Potassium thiocyanate | 0.150 | |
| Sodium hydroxide | 1.000 | |
| | 100.150 | |

The viscosity of this enzymatic adhesive is 900,000 centipoises and the adhesive has an enzymatic shelf life in excess of 2 years.

EXAMPLE 5

This example illustrates an aqueous, enzymatic denture adhesive containing 14 wt. % water together with an enzyme system containing Beta-D-glucose, glucose oxidase, lactoperoxidase and potassium iodide wherein the thickener is a combination of hydrogenated starch, polyacrylic acid (Carbopol 980), and polyvinylpyrrolidone.

| Composition | Weight, grams |
|---|---|
| D.I. Water | 14.000 |
| Glycerine | 14.000 |
| Hydrogenated starch | 62.500 |
| Carbopol 980 | 1.000 |
| Polyvinylpyrollidone | 8.000 |
| Sodium hydroxide | 0.050 |
| Beta-D-glucose | 0.050 |
| Glucose oxidase (100 IU/mg) | 0.008 |
| Lactoperoxidase (100 IU/gm) | 0.010 |
| Potassium iodide | 0.004 |
| | 99.6184 |

The viscosity of this enzymatic adhesive is 1,900,000 centipoises and the adhesive has an enzymatic shelf life in excess of 3 years.

Adjunct antibacterial agents such as the enzyme lysozyme and the protein lactoferrin can also be added to the enzymatic formulations of this invention.

In view of the foregoing description and examples, it will become apparent to those of ordinary skill in the art that equivalent modifications thereof may be made without departing from the spirit and scope of this invention.

That which is claimed is:

1. An aqueous, enzymatic denture adhesive composition having a water content of at least about 10 wt. % and containing, per gram of adhesive, from about 0.015 to about 0.6 millimole of oxidizable substrate and from about 0.5 to about 5,000 International Units of oxidreductase enzyme specific to such substrate for producing hydrogen peroxide upon oral application of the adhesive; and further containing non-toxic, ambient, water soluble thickener in an amount to provide the adhesive with a viscosity from about 300,000 to about 1,900,000 centipoises to thereby stabilize the adhesive against the production of hydrogen peroxide prior to oral application of the adhesive.

2. The denture adhesive of claim 1 wherein the amount of water soluble thickener is so selected as to provide the adhesive with a viscosity from about 400,000 to about 1,750,000 centipoises.

3. The denture adhesive of claim 1 wherein the amount of water soluble thickener is so selected as to provide the adhesive with a viscosity from about 600,000 to about 1,600,000 centipoises.

4. The denture adhesive of claim 1 wherein the upper limit of the water content is about 60 wt. %.

5. The denture adhesive of claim 1 wherein the water content is from about 10 wt. % to about 50 wt. %.

6. The denture adhesive of claim 1 wherein the water content is from about 15 wt. % to about 35 wt. %.

7. The denture adhesive of claim 1 wherein the water soluble thickener is selected from natural and synthetic hydrolloids and mixtures thereof.

8. The denture adhesive of claim 1 wherein the water soluble thickener is a member selected from the group consisting of gum arabic, gum tragacanth, gum karaya, gum guar, xanthan gum, high viscosity starch, hydrogenated starch, carboxymethylcellulose, hydroxymethylcellulose, polyvinylpyrrolidone, polvinyl alcohol, carboxyvinyl polymer, polyacrylic acid, polyacrylamide, ethylene oxide polymers and mixtures thereof.

9. The denture adhesive of claim 1 wherein the oxidizable substrate is Beta-D-glucose and the oxidoreductase enzyme is glucose oxidase.

10. The denture adhesive of claim 1 wherein the oxidizable substrate is hexose and the oxidoreductase enzyme is hexose oxidase.

11. The denture adhesive of claim 1 wherein the oxidizable substrate is present in an amount from about 0.025 to about 0.1 millimole per gram of adhesive and the oxidoreductase enzyme specific to the substrate is present in an amount from about 10 to about 1,000 International Units per gram of adhesive.

12. The denture adhesive of claim 1 which further contains an effective amount of an augmenting anti-bacterial agent selected from the group consisting of lysozyme, lactoferrin and mixtures thereof.

13. The denture adhesive of claim 1 which also contains, per gram of adhesive, from about 0.1 to about 10,000 International Units of peroxidatic peroxidase selected from the group consisting of lactoperoxidase, horse raddish peroxidase, iodide peroxidase, chloride peroxidase, myeloperoxidase and mixtures thereof, and from about 0.0001 to about 0.01 millimole of an alkali metal salt of an oxygen accepting anion selected from the group consisting of thiocyanate, chloride, and iodide and mixtures of such salts for interacting with hydrogen peroxide to produce oxidized anionic bacterial inhibitor.

14. The denture adhesive of claim 13 wherein the peroxidase is present in an amount from about 10 to about 1,500 International Units per gram of adhesive and the oxidizable salt is present in an amount from about 0.001 to about 0.006 millimole per gram of adhesive.

15. The denture adhesive of claim 13 wherein the peroxidase is lactoperoxidase and the alkali metal salt is alkali metal thiocyanate.

16. The denture adhesive of claim 13 wherein the oxidizable substrate is Beta-D-glucose, the oxidoreductase enzyme is glucose oxidase, the peroxide is lactoperoxidase, the oxidizable salt is potassium thiocyanate, and the thickener is a combination of polyvinylpyrrolidone and polyacrylic acid.

* * * * *